(12) United States Patent
Janzadeh et al.

(10) Patent No.: US 10,463,451 B2
(45) Date of Patent: Nov. 5, 2019

(54) SYSTEM AND METHOD FOR MAXIMUM INTERCUSPATION ARTICULATION

(71) Applicant: CLEARCORRECT OPERATING, LLC, Round Rock, TX (US)

(72) Inventors: Hamed Janzadeh, Austin, TX (US); Paul Doan Dinh, Roundrock, TX (US)

(73) Assignee: CLEARCORRECT OPERATING, LLC, Round Rock, TX (US)

( * ) Notice: Subject to any disclaimer, the term of this patent is extended or adjusted under 35 U.S.C. 154(b) by 231 days.

(21) Appl. No.: 15/629,529

(22) Filed: Jun. 21, 2017

(65) Prior Publication Data

US 2017/0360531 A1  Dec. 21, 2017

Related U.S. Application Data

(60) Provisional application No. 62/352,814, filed on Jun. 21, 2016.

(51) Int. Cl.
*A61C 7/00* (2006.01)
*A61C 11/00* (2006.01)
(Continued)

(52) U.S. Cl.
CPC .............. *A61C 7/002* (2013.01); *A61C 11/00* (2013.01); *A61C 13/34* (2013.01); *G06F 16/51* (2019.01);
(Continued)

(58) Field of Classification Search
None
See application file for complete search history.

(56) References Cited

U.S. PATENT DOCUMENTS

| 6,152,731 A | 11/2000 | Jordan et al. |
| 7,077,646 B2 | 7/2006 | Hilliard |

(Continued)

FOREIGN PATENT DOCUMENTS

| EP | 1726265 A1 | 11/2006 |
| WO | 2017223066 A1 | 12/2017 |

OTHER PUBLICATIONS

International Search Report for International Application No. PCT/US2017/038296 dated Aug. 22, 2017.
(Continued)

*Primary Examiner* — Ryan A Jarrett
(74) *Attorney, Agent, or Firm* — Gardella Grace P.A.

(57) ABSTRACT

A system for maximum intercuspation articulation, including a database including patient records and images, and a server in communication with the database and including processing circuitry configured to receive virtual modeling geometrics of two opposing dental models as an input, wherein the two opposing dental models include an upper dental model and a lower dental model of the patient. The processing circuitry is also configured to detect intersection regions between the upper dental model and the lower dental model and perform a simulation on the two opposing dental models, wherein the simulation includes applying simulated physics rules at the two opposing dental models. The processing circuitry is further configured to repeat the detection of the intersection regions and the simulation to generate a maximum intercuspation alignment of the two opposing dental models, mark the intersection regions on the maximum intercuspation alignment, and output the maximum intercuspation alignment.

17 Claims, 5 Drawing Sheets

(51) Int. Cl.
*G06F 17/50* (2006.01)
*G06F 16/51* (2019.01)
*G16H 10/60* (2018.01)
*A61C 13/34* (2006.01)
*G16H 50/50* (2018.01)

(52) U.S. Cl.
CPC ......... *G06F 17/5009* (2013.01); *G16H 10/60* (2018.01); *G16H 50/50* (2018.01)

(56) References Cited

U.S. PATENT DOCUMENTS

| | | | |
|---|---|---|---|
| 8,043,091 B2 | 10/2011 | Schmitt | |
| 8,491,306 B2 | 7/2013 | Raby et al. | |
| 2004/0172150 A1 | 9/2004 | Perot et al. | |
| 2006/0003292 A1* | 1/2006 | Lauren | A61C 5/007 433/215 |
| 2006/0115795 A1* | 6/2006 | Marshall | A61C 13/0004 433/218 |
| 2008/0057466 A1* | 3/2008 | Jordan | A61C 11/00 433/69 |
| 2011/0276159 A1* | 11/2011 | Chun | A61C 11/00 700/98 |
| 2012/0115107 A1 | 5/2012 | Adams | |
| 2016/0051348 A1 | 2/2016 | Boerjes et al. | |

OTHER PUBLICATIONS

Written Opinion for International Application No. PCT/US2017/038296 dated Aug. 22, 2017.
International Preliminary Report on Patentability for International Application No. PCT/US2017/038296 dated Dec. 25, 2018.
Supplementary European Search Report for EP Application No. 17816050.3 dated May 6, 2019.
Examination Report issued in AU Application No. 2017281615 on Jul. 3, 2019.

\* cited by examiner

SYSTEM AND METHOD FOR MAXIMUM INTERCUSPATION ARTICULATION

CROSS-REFERENCE TO RELATED APPLICATION

This application claims the benefit of U.S. Provisional Application No. 62/352,814, filed Jun. 21, 2016.

BACKGROUND

In order to plan an orthodontic treatment for repositioning a patient's teeth, it is often necessary to articulate the patient's arches in digital space to match a same relative alignment as in the patient's mouth. The arches include a maxillary arch and a mandibular arch that make up the top and bottom portions of the patient's mouth, respectively. The maxillary arch is a curved ridge of the upper jaw bone (i.e., the roof of the patient's mouth), whereas the mandibular arch is a curved ridge of the lower jaw bone (i.e., the arch under the patient's tongue). When dental models of the opposing arches are digitally scanned, each model is scanned and saved as a separate virtual model. The digital scans can be used to determine a treatment plan based on the positions of the patient's teeth, as well as the patient's jaw alignment, for example. The scanning of the dental models can be done using existing CAD software to manually articulate the arches and align the models. However, the manual process can be tedious as well as time consuming, and important information regarding the arch alignments may be lost using the existing scanning technologies.

SUMMARY

In an exemplary aspect, a system for maximum intercuspation articulation includes a database including patient records and images, and a server in communication with the database, the server including processing circuitry configured to receive virtual modeling geometries of two opposing dental models as an input, wherein the two opposing dental models include an upper dental model of a patient and a lower dental model of the patient. The processing circuitry is also configured to detect intersection regions between the upper dental model and the lower dental model and perform a simulation on the two opposing dental models, wherein the simulation includes applying simulated physics rules on the two opposing dental models. The processing circuitry is further configured to repeat the detection of the intersection regions and the simulation to generate a maximum intercuspation alignment of the two opposing dental models, mark the intersection regions on the maximum intercuspation alignment, and output the maximum intercuspation alignment.

The foregoing general description of exemplary implementations and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

In the drawings, like reference numerals designate identical or corresponding parts throughout the several views. Further, as used herein, the words "a," "an" and the like generally carry a meaning of "one or more," unless stated otherwise.

Figure 1:
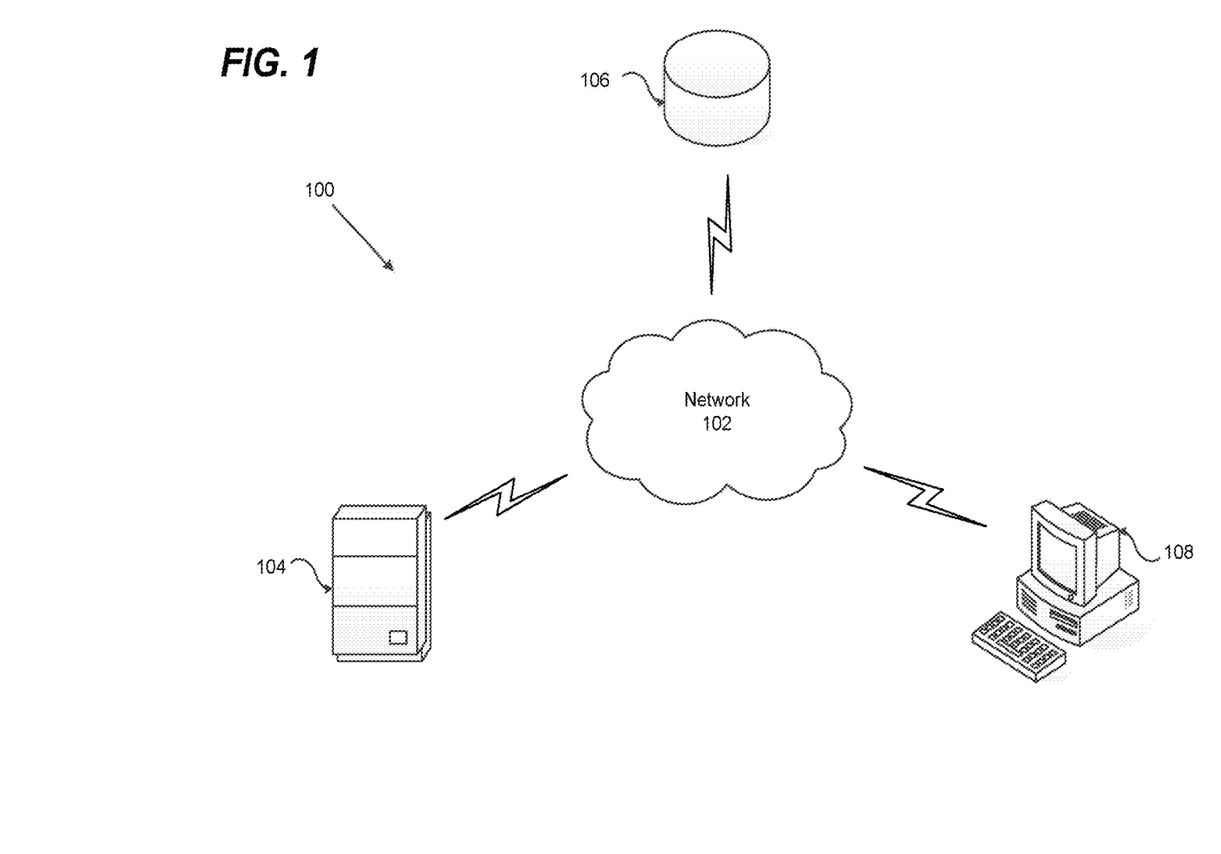
FIG. 1 is a network topology of an exemplary maximum intercuspation articulation system, according to the invention.

The maximum intercuspation alignment system 100 automatically aligns virtually modeled dental models in a digital space. The generation of maximum intercuspation alignment can be utilized in digital scanning devices as a patient's dental structures are initially imaged. The maximum intercuspation alignment system can be utilized in the planning of orthodontic treatment without the need for manual alignment or alterations to the generated maximum intercuspation alignment of the patient's dental structure. As such, the maximum intercuspation alignment system may produce an optimized image of the patient's structure. In some aspects, the maximum intercuspation alignment can be automatically verified and/or optimized via a comparison between the generated maximum intercuspation alignment and records and images of the patient. Additionally, the generated maximum intercuspation alignment may be manually verified and/or optimized by a user.

FIG. 1 is a maximum intercuspation articulation system 100, according to certain exemplary aspects. The maximum intercuspation articulation system 100 can include a server 104, a database 106 and a remote device 108 connected via a network 102. The maximum intercuspation articulation system 100 can be configured to perform an automatic articulation of digital opposing dental arches to maximum intercuspation. As such, the maximum intercuspation articulation system 100 can be configured to automatically align virtually modeled images (e.g., virtual 3D models) of two opposing dental models.

The server 104 represents one or more servers 104 and is connected to the database 106 and the remote device 108 via the network 102. The server 104 includes processing circuitry that can be configured to receive virtual modeling geometrics of two opposing dental models as an input. The virtual modeling geometrics can include 3D geometries of a patient's teeth, for example. The virtual modeling geometrics can be scanned via the remote device 108 such as a scanning device and transmitted to the server 104 via the network 102. The two dental models can include an upper dental model and a lower dental model of a single patient. In some aspects, there may be multiple pairs of dental models for each patient. As such, each upper dental model may correspond to a particular lower dental model. In this instance, each pair of dental models may be timestamped and stored as such in the database 106 to be accessed by the processing circuitry of the server 104.

The processing circuitry can also be configured to detect intersection regions between the upper dental model and the lower dental model. Each intersection region can include a single point, multiple points, a region, multiple regions, and the like. The intersection regions may be detected using virtual modeling intersection detection algorithms, such as 3D intersection detection algorithms, that are performed by the processing circuitry. The processing circuitry can further be configured to perform a simulation on the two opposing dental models (the upper dental model and the lower dental model). In certain aspects, the simulation includes applying simulated physics rules at the two opposing dental models such as pulling forces on the two opposing dental models, pulling forces on one of the two opposing dental models, reactionary forces between the two opposing dental models, and the like. In some aspects, the simulation includes applying simulated physics rules at the intersection regions of the two opposing dental models. The simulated physics rules can be utilized to align the two opposing dental models under simulations of realistic, physical conditions. The simulated physics rules can also be utilized by the processing circuitry to maneuver the two opposing dental models such that maximum intercuspation is ultimately achieved. For example, the pulling forces on one of the two opposing dental models can simulate an elastic band pulling the upper dental model down toward the lower dental model. The simulation can include, for example, a hook in the center of the upper dental model such that the elastic band can be hooked to the hook which would pull the upper dental model toward the lower dental model when the other end of the elastic band was also hooked to a hook in the center of the lower dental model. Alternatively, or additionally, the elastic band can also pull the lower dental model toward the upper dental model. The connection points being in the center of each dental model can allow the dental models to pivot around the connection point.

In certain aspects, the simulation also includes a vibration of the upper dental model. The vibration can include a predetermined frequency and amplitude that is utilized to optimize the maximum intercuspation. Additionally, the predetermined amplitude of the vibration can be reduced over a predetermined period of time and diminish away as the simulation continues over the period of time. As such, the vibration of the upper dental model can simulate realistic conditions of the alignment of a patient's teeth in that the vibration prevents the upper dental model from getting stuck in a local extrema and may ultimately allow for the generation of a deeper bite alignment. In an embodiment, the upper and/or lower dental model can be shifted back and forth where digital intersections can be detected and adjustments can be made based on the digital intersections.

The processing circuitry can further be configured to repeat the detection of the intersection regions and the simulation to generate a maximum intercuspation alignment of the two opposing dental models. The processing circuitry can also be configured to mark the intersection regions on top of the maximum intercuspation alignment as it is been generated. For example, the markings can include blue colored spots on top of the virtual modeling teeth geometries once they have reached maximum intercuspation. As such, the processing circuitry can output the maximum intercuspation alignment including the virtual modeling teeth geometries and the corresponding markings. The maximum intercuspation can be graphically displayed at the remote device 108 via CAD software, or any other graphical software that is known.

The database 106 represents one or more databases 106, and is connected to the server 104 and the remote device 108 via the network 102. The database can be utilized to provide patient records and images corresponding to the patient records to be accessed by the processing circuitry of the server 104.

The remote device 108 represents one or more remote devices 108, and is connected to the server 104 and the database 106 via the network 102. The remote device 108 can include a computer, a tablet, a smartphone, and the like. The remote device 108 can be utilized to provide manual inputs to adjust the dental models. Additionally, the remote device 108 can be utilized to provide a manual restart of the detection of the intersection regions and of the simulation. Further, the remoted device 108 may be utilized for viewing the patient records, patient images, virtually modeled dental models, and the like.

The network 102 represents one or more networks 102, and is connected to the server 104, the database 106 and the remote device 108. The network 102 can communicate via wired networks such as Ethernet, LAN or any other wired form of communication that is known. The network 102 can also communicate via wireless networks such as Wi-Fi, BLUETOOTH, cellular networks including EDGE, 3G, 4G and LTE wireless cellular systems, Infrared or any other wireless form of communication that is known. The network 102 can provide a secure connection so that the data exchanged between the server 104, the database 106, and the remote device 108 may be encrypted. Of course, one of ordinary skill will recognize that the network 102 may also include a combination of the wired and wireless networks described above.

Figure 2:
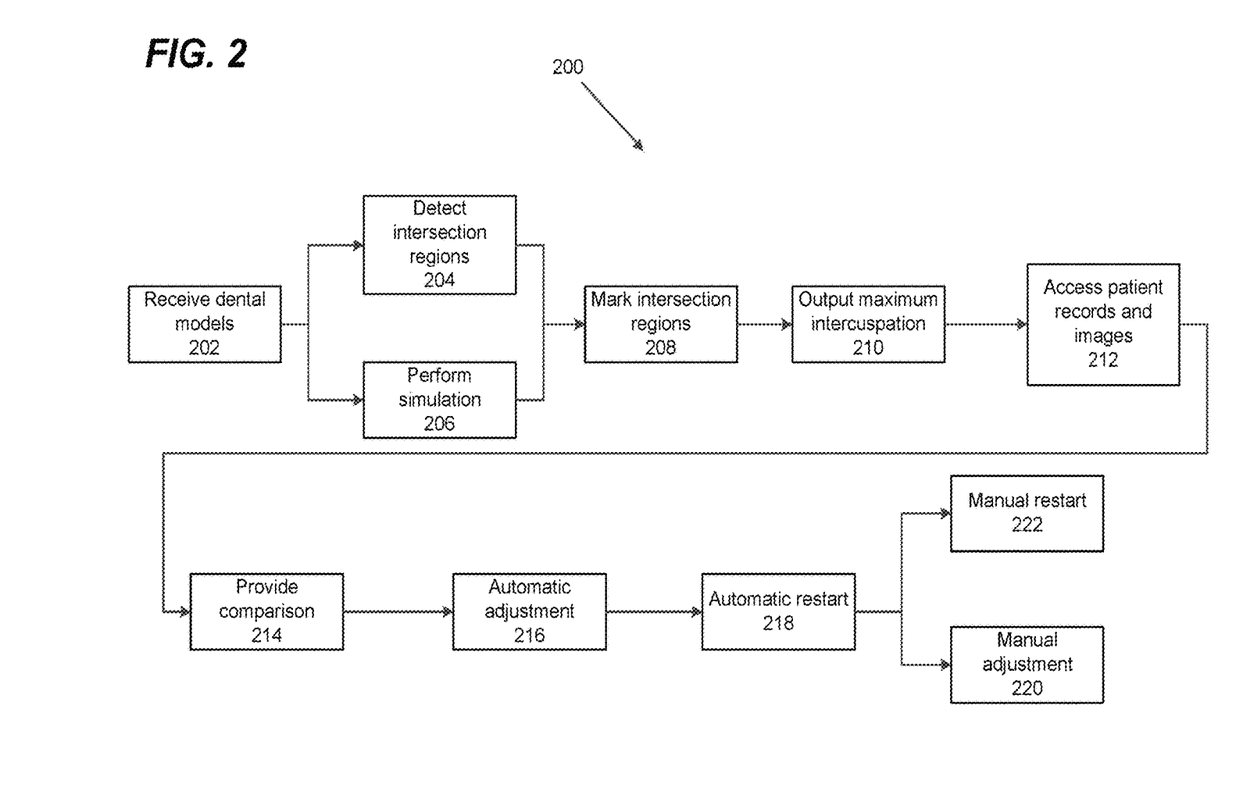
FIG. 2 is an exemplary workflow of the maximum intercuspation articulation system of FIG. 1.

FIG. 2 is maximum intercuspation articulation workflow 200, according to certain exemplary aspects. The maximum intercuspation articulation workflow 200 describes the generation and the verification of an automatic maximum intercuspation articulation. The maximum intercuspation articulation workflow 200 can include receiving dental models 202, detecting intersection regions of the dental models 204, performing a simulation 206, marking the intersection regions 208, and outputting the maximum intercuspation alignment 210. The maximum intercuspation articulation workflow 200 can also include accessing patient records and images 212, providing a comparison between the maximum intercuspation alignment and the patient records and images 214, automatically adjusting the maximum intercuspation alignment 216, and automatically restarting the detection of the intersection regions and the simulation 218. The maximum intercuspation articulation workflow 200 can further include a manual restart of the detection of the intersection regions and the simulation 220 and a manual adjustment of the maximum intercuspation alignment 222.

Processing circuitry of a server 104 can be configured to receive virtually modeled dental models of a patient 202. The virtual modeling dental models can include an upper dental model and a lower dental model. The virtual modeling dental models can include teeth and gums corresponding to the each dental model. The virtual modeling dental models can be received in a virtual modeling geometric format, such as 3D, to be processed by the processing circuity of the server. In some aspects, the virtual modeling dental models are processed into virtual modeling geometric formats by the processing circuitry of the server 106. The processing circuitry can be configured to detect intersection regions of each pair of upper and lower dental models 204. The intersection regions can include one or more regions, points, or both. In certain aspects, the intersection regions can be utilized by the processing circuitry to specify regions in which a simulation will be performed 206. The simulation can be performed 206 at the intersection regions, at each upper dental model, at each lower dental model, or any combination thereof. The simulated physics rules can be utilized to align the two opposing dental models under realistic, physical conditions. The simulated physics rules can also be utilized by the processing circuitry to maneuver the two opposing dental models such that maximum intercuspation between the upper dental model and the lower dental model is ultimately achieved.

When maximum intercuspation of the two dental models is achieved, the processing circuitry can be configured to mark the intersection regions 208 at the maximum intercuspation. For example, the markings can include blue colored spots on top of the virtual modeling dental geometries once they have reached maximum intercuspation. As such, the processing circuitry can output the maximum intercuspation alignment 210 including the virtual modeling dental geometries and the corresponding markings. The processing circuitry can also be configured to access patient records and images 212 at a database 106 in communication with the server 104 via the network 102. The patient records and images can be utilized by the processing circuitry to provide a comparison between the patient records and images and the maximum intercuspation alignment 214. The comparison can be provided by the processing circuitry 214 to distinguish the differences between the dental structures of the patient in real time versus the simulated event of maximum intercuspation alignment.

The processing circuitry can further be configured to automatically adjust the maximum intercuspation alignment based on the comparison 216. In this instance, the processing circuitry may utilize predetermined alignment conditions to evaluate the differences between the dental structures of the patient and the simulated event of maximum intercuspation alignment. Additionally, the processing circuitry can be configured to restart the detection of intersection regions and the simulation automatically 218. As such, the processing circuitry may determine that the automatic restart 218 is necessary when the comparison does not satisfy the predetermined alignment condition.

In some aspects, the processing circuitry can be configured to receive a second input corresponding to a manual adjustment of the dental models 220. The manual adjustment 220 can include an adjustment to the dental models, an adjustment to the intersection regions, and the like. The manual adjustment 220 can be made to the virtual modeling dental geometries initially when they are received by the processing circuitry, during the simulation, once maximum intercuspation alignment is achieved, or any combination thereof. The manual adjustment 220 can be utilized by a user to verify the accuracy of the automatic maximum intercuspation alignment. The processing circuitry can further be configured to receive a third input corresponding to a manual restart 222 of the detection of the intersection regions and the simulation. The manual restart 222 may be made at any point during the maximum intercuspation alignment workflow 200. The manual restart 222 can be utilized by a user to verify the accuracy of the automatic maximum intercuspation alignment.

Figure 3:
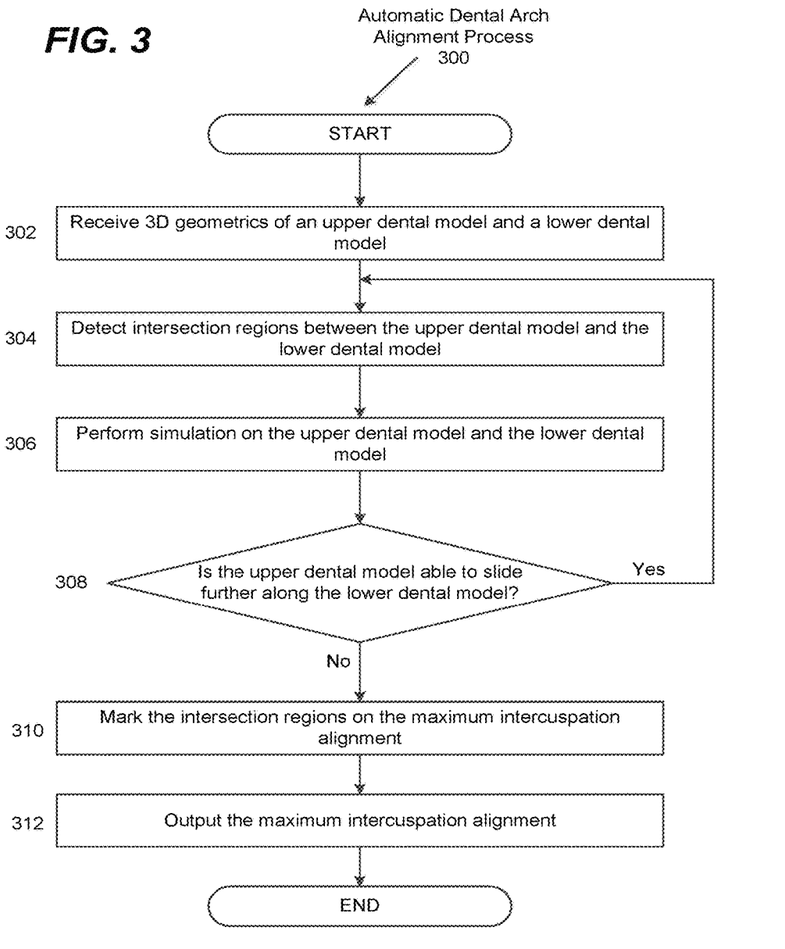
FIG. 3 is a flowchart of an exemplary maximum intercuspation articulation process.

FIG. 3 is a maximum intercuspation articulation process 300, according to certain exemplary aspects. The maximum intercuspation articulation process 300 describes a process of automatically aligning two opposing dental models at maximum intercuspation. At step 302, processing circuitry of a server 104 is configured to receive virtual modeling geometrics of an upper dental model and a lower dental model. The virtual modeling geometrics can include a scanned virtually modeled image, such as a 3D image, of the upper dental model of a patient and the lower dental model of the patient. The upper dental model and the lower dental model can each include corresponding gums and teeth of the patient. In certain aspects, the teeth of the patient is scanned at the maximum intercuspation articulation system 100 and processed therein. In other aspects, the teeth of the patient is scanned at a remote device 108 and then received at the maximum intercuspation articulation system 100 to be processed by the processing circuitry of the server 104.

At step 304, the processing circuitry is configured to detect intersection regions between the upper dental model and the lower dental model. The intersection regions can include one or more regions, points, or both, at the two dental models. In some aspects, the intersection regions are detected by the processing circuitry utilizing virtual modeling intersection detection algorithms, such as 3D intersection detection algorithms, for example.

At step 306, the processing circuitry is configured to perform a simulation on the upper dental model and the lower dental model. The simulation includes applying simulated physics rules at the two opposing dental models such as pulling forces on the two opposing dental models, pulling forces on one of the two opposing dental models, reactionary forces between the two opposing dental models, and the like. In some aspects, the simulation includes applying simulated physics rules at the intersection regions of the two opposing dental models. The simulated physics rules can be utilized to align the two opposing dental models under simulations of realistic, physical conditions. The simulated physics rules can also be utilized by the processing circuitry to maneuver the two opposing dental models such that maximum intercuspation is ultimately achieved. In some aspects, the simulation includes fixing the position of the lower dental model and sliding the upper dental model over the fixed, lower dental model. In this instance, the upper dental model is moveable and actuated by forces of the simulated physics rules to slide on top of the lower dental model.

At step 308, a determination is made of whether the upper dental model is able to slide further along the lower dental model. As such, when the upper model is unable to slide further along the lower dental model, it may be determined that the dental models have reached maximum intercuspation alignment. In certain aspects, the upper dental model is actuated by a vibration to achieve a deeper bite alignment. The vibration can include a predetermined frequency and amplitude that is utilized to optimize the maximum intercuspation. Additionally, the predetermined amplitude of the vibration can be reduced over a predetermined period of time and diminish as the simulation continues over the period of time. The vibration of the upper dental model can simulate realistic conditions of the alignment of a patient's teeth in that the vibration prevents the upper dental model from getting stuck in a local extrema and may ultimately allow for the simulation of a deeper bite alignment. If the processing circuitry determines that the upper dental model is unable to slide further along the lower dental model, resulting in a "no" at step 308, the maximum intercuspation articulation process 300 proceeds to step 310 as a maximum intercuspation alignment is generated. Otherwise, if the processing circuitry determines that the upper dental model is able to slide further along the lower dental model, resulting in a "yes" at step 308, the maximum intercuspation articulation process proceeds to step 304.

At step 310, the processing circuitry is configured to mark the intersection regions on the maximum intercuspation alignment. In other words, when maximum intercuspation of the two dental models is achieved, the processing circuitry can be configured to mark the intersection regions at the maximum intercuspation alignment. For example, the markings can include blue colored spots on top of the virtual modeling dental geometries once they have reached maximum intercuspation alignment.

At step 312, the processing circuitry is configured to output the maximum intercuspation alignment. As such, the processing circuitry can output the maximum intercuspation alignment including the virtual modeling dental geometries and the corresponding markings. In some aspects, the maximum intercuspation alignment can be graphically displayed at a remote device 108 via CAD software, or any other graphical software that is known. In certain aspects, the maximum intercuspation alignment can be stored in the database 106 and associated with corresponding patient records and images.

Figure 4:
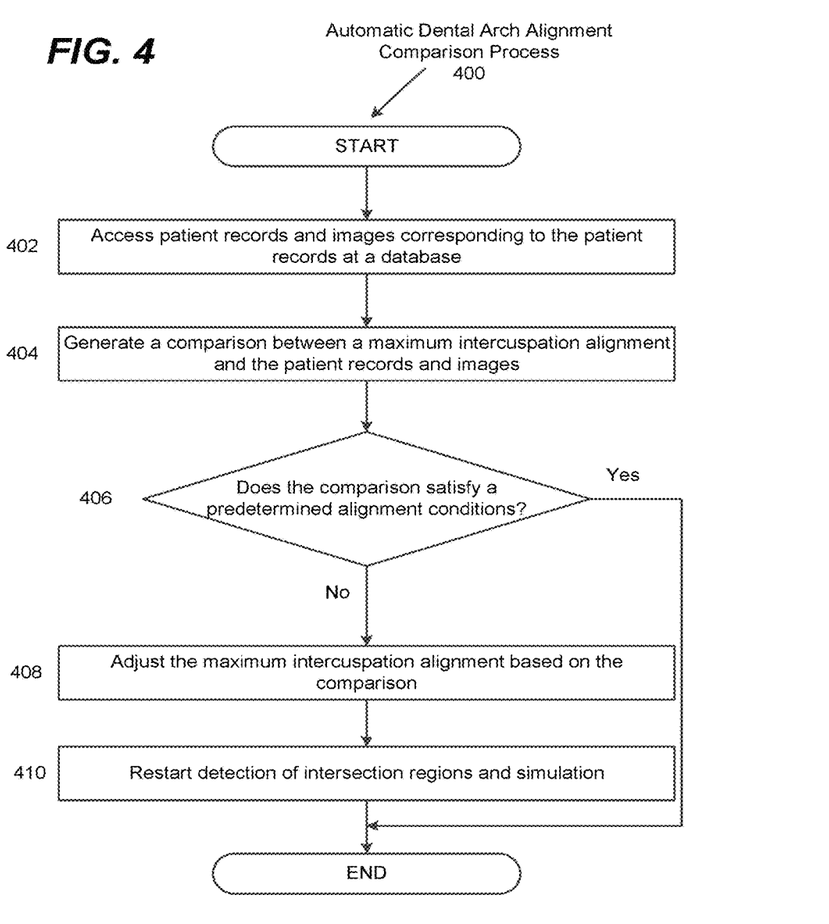
FIG. 4 is a flowchart of an exemplary maximum intercuspation articulation comparison process.

FIG. 4 is a maximum intercuspation articulation comparison process 400, according to certain exemplary aspects. The maximum intercuspation articulation comparison process 400 describes a process of comparing an automatically generated maximum intercuspation alignment with patient records and images. At step 402, processing circuitry of a server 104 can be configured to access patient records and images corresponding to the patient records at a database 106. The patient records and images can include information pertaining to teeth of a patient, gums of a patient, present orthodontic treatment, planned orthodontic treatment, the current state of the patient's mouth, and the like.

At step 404, the processing circuitry can be configured to generate a comparison between a maximum intercuspation alignment and corresponding patient records and images. The maximum intercuspation alignment can include an automatically generated virtual modeling image of the corresponding patient's dental structures at maximum intercuspation. The comparison can be provided by the processing circuitry to distinguish differences between the dental structures of the patient in real time and the automatic generation of maximum intercuspation alignment of the corresponding dental structures.

At step 406, a determination is made of whether the comparison satisfies a predetermined alignment conditions. As such, the processing circuitry may utilize predetermined alignment conditions to evaluate the differences between the dental structures of the patient and the simulated event of maximum intercuspation alignment. If the processing circuitry determines that the comparison does not satisfy the predetermined alignment conditions, resulting in a "no" at step 406, the maximum intercuspation articulation comparison process 400 proceeds to step 408. Otherwise, if the processing circuitry determines that the comparison does satisfy the predetermined alignment conditions, resulting in a "yes" at step 406, the maximum intercuspation articulation comparison process 400 ends.

At step 408, the processing circuitry can be configured to automatically adjust the maximum intercuspation alignment based on the comparison. The automatic adjustment can include an adjustment to the dental models, an adjustment to intersection regions of the dental models, and the like. The automatic adjustment can be made to the virtual modeling dental geometries initially, during the simulation, once maximum intercuspation alignment is achieved, or any combination thereof.

At step 410, the processing circuitry can be configured to restart the detection of intersection regions and the simulation involved in the generation of the maximum intercuspation alignment. In certain aspects, the processing circuitry can be configured to proceed to the maximum intercuspation articulation process 300 so that new intersection points may be determined and the simulation may be run again. In other aspects, the processing circuitry can be configured to generate a second comparison between the automatically adjusted maximum intercuspation alignment and the patient records and images. As such, the processing circuitry can utilize the second comparison to determine whether the second comparison satisfies the predetermined alignment conditions.

Figure 5:
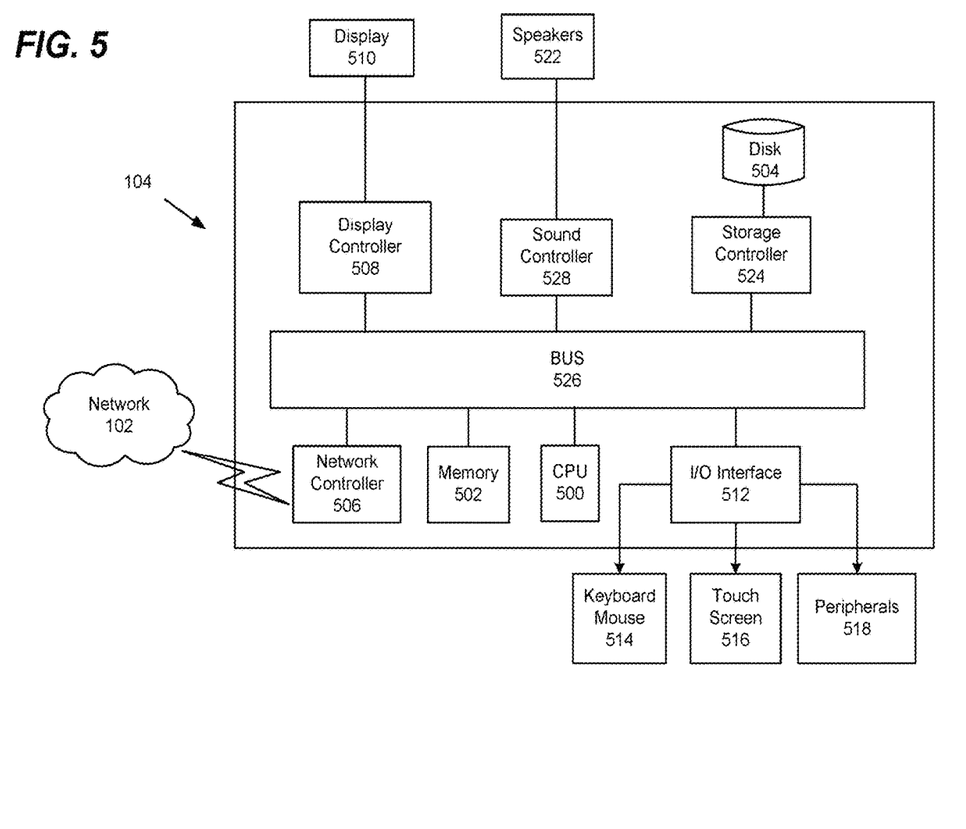
FIG. 5 is a hardware block diagram of a server, according to certain exemplary aspects.

FIG. 5 is a hardware block diagram of a server, according to certain exemplary aspects. In FIG. 5, the server 104 includes a CPU 500 which performs the processes described above/below. The process data and instructions may be stored in memory 502. These processes and instructions may also be stored on a storage medium disk 504 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 104 communicates, such as another server or computer.

Further, the claimed advancements may be provided as a utility application, background daemon, or component of an operating system, or combination thereof, executing in conjunction with CPU 500 and an operating system such as Microsoft Windows 7, UNIX, Solaris, LINUX, Apple MAC-OS and other systems known to those skilled in the art.

The general purpose storage controller 524 connects the storage medium disk 5504 with communication bus 526, which may be an ISA, EISA, VESA, PCI, or similar, for interconnecting all of the components of the server 104. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time. Additionally, some implementations may be performed on modules or hardware not identical to those described. Accordingly, other implementations are within the scope that may be claimed.

The above-described hardware description is a non-limiting example of corresponding structure for performing the functionality described herein.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, an implementation may be performed on modules or hardware not identical to those described. Accordingly, other implementations are within the scope that may be claimed.

The invention claimed is:

1. A system for maximum intercuspation articulation, comprising:
    a database including patient records and images corresponding to the patient records; and
    a server in communication with the database, the server including processing circuitry configured to:
    receive virtual modeling geometrics of two opposing dental models as an input,
    wherein the two opposing dental models include an upper dental model of a patient and a
    lower dental model of the patient,
    detect one or more intersection regions between the upper dental model and the lower dental model,
    perform a simulation on the two opposing dental models, wherein the simulation includes applying simulated physics rules at the one or more intersection regions between the two opposing dental models, wherein the physics rules include vibration of the upper dental model to optimize a maximum intercuspation alignment, the vibration including a predetermined frequency and a predetermined amplitude,
    repeat the detection of the one or more intersection regions and the simulation to generate the maximum intercuspation alignment of the two opposing dental models,
    mark the one or more intersection regions on the maximum intercuspation alignment, and
    output the maximum intercuspation alignment.

2. The system for maximum intercuspation articulation of claim 1, wherein the lower dental model is fixed and the upper dental model is moveable and actuated by forces of the simulated physics rules to slide on top of the lower dental model.

3. The system for maximum intercuspation articulation of claim 2, wherein the processing circuitry is further configured to repeat the detection of the one or more intersection regions and the simulation until the upper dental model is actuated by the forces of the simulated physics rules and unable to slide further over the lower dental model.

4. The system for maximum intercuspation articulation of claim 1, wherein the predetermined amplitude is reduced over a predetermined period of time.

5. The system for maximum intercuspation articulation of claim 1, wherein the processing circuitry is further configured to receive a second input including a manual adjustment of the two opposing dental models.

6. The system for maximum intercuspation articulation of claim 1, wherein the processing circuitry is further configured to receive a third input including a manual restart of the detection of the one or more intersection regions and the simulation.

7. The system for maximum intercuspation articulation of claim 1, wherein the processing circuitry is further configured to:
    access the patient records and the images corresponding to the patient records at the database;
    generate a comparison between the maximum intercuspation alignment and the patient records and the images corresponding to the patient records; and
    adjust the maximum intercuspation alignment based on the comparison.

8. The system for maximum intercuspation articulation of claim 7, wherein the processing circuitry is further configured to automatically restart the detection of the one or more intersection regions and the simulation when the comparison does not satisfy a predetermined alignment condition.

9. A method for maximum intercuspation articulation, comprising:
    receiving virtual modeling geometrics of two opposing dental models as an input, wherein the two opposing dental models include an upper dental model of a patient and a lower dental model of the patient;
    detecting, via processing circuitry of a server, one or more intersection regions between the upper dental model and the lower dental model;
    performing, via the processing circuitry, a simulation on the two opposing dental models, wherein the simulation includes applying simulated physics rules at the one or more intersection regions between the two opposing dental models, wherein the physics rules include vibration of the upper dental model to optimize a maximum intercuspation alignment, the vibration including a predetermined frequency and a predetermined amplitude;
    repeating the detection of the one or more intersection regions and the simulation to generate the maximum intercuspation alignment of the two opposing dental models;
    marking, via the processing circuitry, the one or more intersection regions on the maximum intercuspation alignment; and
    outputting, via the processing circuitry, the maximum intercuspation alignment.

10. The method claim 9, wherein the lower dental model is fixed and the upper dental model is moveable and actuated by forces of the simulated physics rules to slide on top of the lower dental model.

11. The method of claim 10, further comprising
    repeating the detection of the one or more intersection regions and the simulation until the upper dental model is actuated the forces of the simulated physics rules and unable to slide further over the lower dental model.

12. The method of claim 9, wherein the predetermined amplitude is reduced over a predetermined period of time.

13. The method of claim 9, further comprising
    receiving a second input including a manual adjustment of the two opposing dental models.

14. The method of claim 9, further comprising
    receiving a third input including a manual restart of the detection of the one or more intersection regions and the simulation.

15. The method of claim 9, further comprising:
    accessing patient records and images corresponding to the patient records at a database in communication with the server;

generating a comparison between the maximum intercuspation alignment and the patient records and the images corresponding to the patient records of the database; and adjusting the maximum intercuspation alignment based on the comparison.

16. The method of claim 15, further comprising
restarting the detection of the one or more intersection regions and the simulation automatically when the comparison does not satisfy a predetermined alignment condition.

17. A non-transitory computer-readable medium having instructions stored thereon that, when executed by a processor, cause the processor to perform a method comprising:

receive virtual modeling geometrics of two opposing dental models as an input, wherein the two opposing dental models include an upper dental model of a patient and a lower dental model of the patient;

detect one or more intersection regions between the upper dental model and the lower dental model;

perform a simulation on the two opposing dental models, wherein the simulation includes applying simulated physics rules at the one or more intersection regions between the two opposing dental models, wherein the physics rules include vibration of the upper dental model to optimize a maximum intercuspation alignment, the vibration including a predetermined frequency and a predetermined amplitude;

repeat the detection of the one or more intersection regions and the simulation to generate the maximum intercuspation alignment of the two opposing dental models;

marking the one or more intersection regions on the maximum intercuspation alignment; and output the maximum intercuspation alignment.

* * * * *